United States Patent
Nelson (10) Patent No.: US 7,186,958 B1
(45) Date of Patent: Mar. 6, 2007

(54) INHALER

(75) Inventor: Stephen G. Nelson, San Diego, CA (US)

(73) Assignee: Zhao Wei, LLC, San Diego, CA (US)

( * ) Notice: Subject to any disclaimer, the term of this patent is extended or adjusted under 35 U.S.C. 154(b) by 0 days.

(21) Appl. No.: 11/322,956

(22) Filed: Dec. 30, 2005

Related U.S. Application Data (60) Provisional application No. 60/713,611, filed on Sep. 1, 2005.

(51) Int. Cl.
*H05B 3/06* (2006.01)

(52) U.S. Cl. .................. 219/533; 219/486; 219/521; 128/203.26; 128/200.24; 128/200.23

(58) Field of Classification Search ............. 219/533, 219/486, 521; 128/200.14, 200.23, 200.24, 128/200.26, 200.27
See application file for complete search history.

(56) References Cited

U.S. PATENT DOCUMENTS

| | | | |
|---|---|---|---|
| 3,115,134 A * | 12/1963 | Schmahl ............... | 128/203.27 |
| 4,735,217 A | 4/1988 | Gerth et al. | |
| 5,564,442 A | 10/1996 | MacDonald et al. | |
| 5,595,706 A | 1/1997 | Sikka et al. | |
| 5,620,651 A | 4/1997 | Sikka et al. | |
| 5,743,251 A | 4/1998 | Howell et al. | |
| 5,976,458 A | 11/1999 | Sikka et al. | |
| 5,993,748 A | 11/1999 | Wheeler | |
| 6,030,472 A | 2/2000 | Hajaligol et al. | |
| 6,033,623 A | 3/2000 | Deevi et al. | |
| 6,143,241 A | 11/2000 | Hajaligol et al. | |
| 6,214,133 B1 | 4/2001 | Deevi et al. | |
| 6,234,167 B1 | 5/2001 | Cox et al. | |
| 6,280,682 B1 | 8/2001 | Sikka et al. | |
| 6,284,191 B1 | 9/2001 | Deevi et al. | |
| 6,293,987 B1 | 9/2001 | Hajaligol et al. | |
| 6,294,130 B1 | 9/2001 | Hajaligol et al. | |
| 6,332,936 B1 | 12/2001 | Hajaligol et al. | |
| 6,368,406 B1 | 4/2002 | Deevi et al. | |
| 6,425,964 B1 | 7/2002 | Deevi et al. | |
| 6,443,146 B1 * | 9/2002 | Voges ................... | 128/200.14 |

(Continued)

OTHER PUBLICATIONS

O'Connell, Vanessa, Rx From Marlboro Man: Device That Delivers Drugs, Not Smoke, Wall Street Journal, Oct. 27, 2005, Dow Jones & Company, Inc., New York, NY.

*Primary Examiner*—Robin Evans
*Assistant Examiner*—Leonid M. Fastovsky
(74) *Attorney, Agent, or Firm*—SoCal IP Law Group LLP; Steven C. Sereboff (57) ABSTRACT

There is an apparatus having a housing, a heating element, a heating element switch, a heating chamber, a heating chamber cover, and a controller. The housing is handheld. The heating element is disposed within the housing. The heating element switch may be electrically coupled with the heating element. The heating chamber is disposed within the housing. The heating chamber cover may be adapted to at least partially eject the heating chamber from the housing when the heating chamber cover is displaced relative to the housing. The controller is electrically coupled with the heating element switch. The controller is adapted to control a transfer of energy to the heating element. The controller may be adapted to prevent the transfer of energy to the heating element if the heating chamber cover is not in a closed position relative to the housing.

10 Claims, 8 Drawing Sheets

U.S. PATENT DOCUMENTS

| | | |
|---|---|---|
| 6,489,043 B1 | 12/2002 | Deevi et al. |
| 6,491,233 B2 | 12/2002 | Nichols |
| 6,501,052 B2 | 12/2002 | Cox et al. |
| 6,506,338 B1 | 1/2003 | Gedevanishvili et al. |
| 6,513,524 B1 * | 2/2003 | Storz .................. 128/203.26 |
| 6,516,796 B1 | 2/2003 | Cox et al. |
| 6,532,965 B1 | 3/2003 | Abhulimen et al. |
| 6,557,552 B1 | 5/2003 | Cox et al. |
| 6,568,390 B2 | 5/2003 | Nichols et al. |
| D478,983 S | 8/2003 | Whitehall |
| 6,607,576 B1 | 8/2003 | Sikka et al. |
| 6,640,050 B2 | 10/2003 | Nichols et al. |
| 6,660,109 B2 | 12/2003 | Hajaligol et al. |
| 6,681,769 B2 | 1/2004 | Sprinkel, Jr. et al. |
| 6,681,998 B2 | 1/2004 | Sharpe et al. |
| 6,685,882 B2 | 2/2004 | Deevi |
| 6,701,921 B2 | 3/2004 | Sprinkel |
| 6,701,922 B2 | 3/2004 | Hindle |
| 6,715,487 B2 | 4/2004 | Nichols |
| 6,746,508 B1 | 6/2004 | Deevi |
| 6,761,164 B2 * | 7/2004 | Amirpour et al. ..... 128/203.26 |
| 6,766,220 B2 | 7/2004 | McRae |
| 6,772,756 B2 * | 8/2004 | Shayan ................ 128/203.26 |
| 6,772,757 B2 | 8/2004 | Sprinkel |
| 6,799,572 B2 | 10/2004 | Nichols |
| 6,804,458 B2 | 10/2004 | Sherwood |
| 6,830,676 B2 | 12/2004 | Deevi |
| 6,854,461 B2 | 2/2005 | Nichols |
| 6,883,516 B2 | 4/2005 | Hindle |
| 6,923,179 B2 | 8/2005 | Gupta |
| 6,946,097 B2 | 9/2005 | Deevi |
| D512,777 S | 12/2005 | Beisner |
| 7,040,314 B2 | 5/2006 | Nguyen |
| 7,077,130 B2 | 7/2006 | Nichols |
| 2003/0106551 A1 | 6/2003 | Sprinkel |
| 2003/0132219 A1 | 7/2003 | Cox |
| 2003/0230303 A1 | 12/2003 | Nichols |
| 2004/0016427 A1 | 1/2004 | Bryon |
| 2004/0050383 A1 | 3/2004 | Cox |
| 2004/0065324 A1 * | 4/2004 | Pivinski ................ 128/200.23 |
| 2004/0129793 A1 | 7/2004 | Nguyen |
| 2004/0151670 A1 | 8/2004 | Blondino |
| 2004/0154701 A1 | 8/2004 | Lu |
| 2004/0170405 A1 | 9/2004 | Sherwood |
| 2004/0182389 A1 | 9/2004 | Sprinkel |
| 2004/0211418 A1 | 10/2004 | Shayan |
| 2004/0223917 A1 | 11/2004 | Hindle |
| 2004/0223918 A1 | 11/2004 | Pham |
| 2004/0255941 A1 | 12/2004 | Nichols |
| 2004/0265519 A1 | 12/2004 | Pellizzari |
| 2005/0045179 A1 | 3/2005 | Faison |
| 2005/0079137 A1 | 4/2005 | Blondino |
| 2005/0132879 A1 | 6/2005 | Grollimund |
| 2005/0133029 A1 | 6/2005 | Nichols |
| 2005/0143866 A1 | 6/2005 | McRae |
| 2005/0279353 A1 * | 12/2005 | McCoy ................ 128/200.24 |
| 2006/0037432 A1 | 2/2006 | Deevi |
| 2006/0047368 A1 | 3/2006 | Maharajh |
| 2006/0102175 A1 * | 5/2006 | Nelson ................ 128/200.24 |

\* cited by examiner

INHALER

RELATED APPLICATION INFORMATION

This application claims priority from Provisional Application No. 60/713,611, filed Sep. 1, 2005, which is incorporated herein by reference.

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by anyone of the patent disclosure as it appears in the Patent and Trademark Office patent files or records, but otherwise reserves all copyright and trade dress rights whatsoever.

BACKGROUND

1. Field

This disclosure relates to inhaling devices.

2. Description of the Related Art

Herbs and botanicals have been used for thousands of years by both ancient and modern civilizations. Aromatherapy, herbology, and phyto-inhalation products are popular among many people.

At least a billion people worldwide smoke tobacco and other phyto materials. However, because of health considerations or various laws and regulations, smoking is now prohibited in many airplanes, restaurants and other public places.

Products are now being introduced to deliver the pleasures of smoking without polluting the environment. Examples of such products include nicotine chewing gum and patches.

DETAILED DESCRIPTION

Throughout this description, the embodiments and examples shown should be considered as exemplars, rather than limitations on the apparatus and methods disclosed or claimed.

Description of Systems

Figure 1:
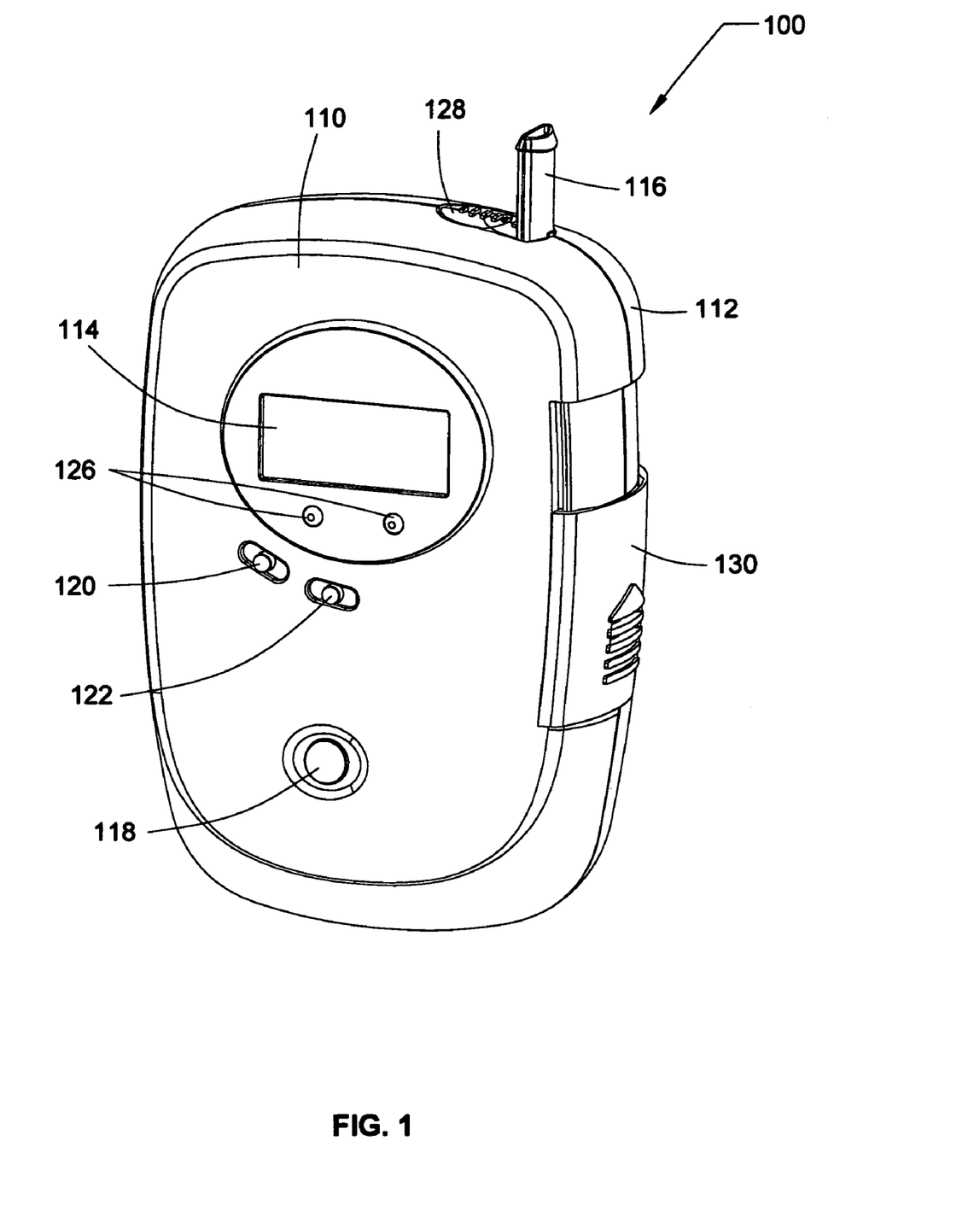
FIG. 1 is a front perspective view of an inhaler.

Referring now to FIG. 1, there are shown a front perspective view of a volatizing device 100. The term volatize refers to causing a material to evaporate, become volatile, become a vapor or be carried by a vapor. The volatizing device 100 may be designed to volatize a phyto material. The term phyto refers to a plant. The term plant refers to any organism constituting the kingdom Plantae.

In general, volatizing devices volatize a substance. Essential components of such substances are commonly referred to by the coined terms substituent or constituent. However, as used herein, the term constituent refers only to a phyto material or an essential oil.

The volatizing device 100 may include a front housing 110, a rear housing 112, a display 114, a mouthpiece 116, a power button 118, a temperature increase button 120, a temperature decrease button 122, two indicator lights 126, a mouthpiece cover 128, a mouthpiece slider 129, and a heating chamber cover 130.

The term housing refers to a structure that at least partially covers, protects, or encloses a device. As assembled, the front housing 110 and the rear housing 112 may provide a structure for the volatizing device 100. The volatizing device 100 may be designed to be handheld. The term handheld refers to a device that is designed to be operated while held in the hand of a person. A handheld device may be held and operated in one hand, or may be held with one hand and operated with a second hand, or may be held in one hand and operated in another fashion. A handheld device may be portable, fit within a person's shirt pocket, slacks pocket, purse, or handbag. Additionally, a handheld device may be adapted to be secured to something (e.g., a wristband or a belt) via a clip, an adhesive, a Velcro® type hook and loop fastener, or other securing device. A handheld device is typically lightweight. Thus, the volatizing device 100 is both portable and designed for privacy.

For example, the dimensions of the volatizing device 100 may be 3 inches in width, 4 inches in length and 1 inch in depth or other dimensions. The front housing 110, rear housing 112, mouthpiece 116, mouthpiece cover 128 and heating chamber cover 130 may include a plastic material, a metal material, a composite material, a ceramic material and/or combinations thereof.

The materials selected for the components of the volatizing device 100 may be determined based on cost of manufacture, life cycle durability, vibration and shock resistance, resistance to deformation based on heat, and other factors. In order to prevent lacerations of a person's skin or clothing, the exterior surfaces of the volatizing device 100 may be beveled, rounded, and/or relatively smooth. In order to prevent discomfort and/or burns to a person's skin or clothing, the components of the volatizing device 100 may include heat insulating features. For example, the interior of the volatizing device features may include an insulating foam fill. Additional insulating features may include surface coatings and/or treatments such as powder coating and or paints utilizing ceramic and/or other insulating materials.

The term mouthpiece refers to a portion of an apparatus adapted both to allow a fluid to flow there through and at least partially fit on or within a mouth of a person or mammal. The mouthpiece 116 may at least partially define a cavity. The term cavity refers to a hollow space at least partially surrounded by a housing. The mouthpiece 116 may include a material selected to be comfortable, both in texture and taste to a person's lips and tongue. The mouthpiece 116 may have dimensions of ¾ inches in width, ½ inch in depth and 2 inches in length, or other dimensions. The mouthpiece 116 may be disposed at a position which is both comfortable for a person to hold the volatizing device 110 and inhale a volatized material from the mouthpiece 116.

The mouthpiece 116 may be adapted to be at least partially retractable into the volatizing device 116. In a retracted position, the mouthpiece cover 128 may be displaced to cover, hide and/or protect the mouthpiece 116. The term displace refers to the act of physically shifting, sliding, moving, or rotating something. For example, the mouthpiece may slide and/or rotate to a position within the volatizing device 116.

In turn, the mouthpiece cover 128 may be slid, shifted, and/or rotated to hide the mouthpiece 116. By enclosing the mouthpiece 116, germs, debris or other undesirable substances may be prevented from building up on the mouthpiece 116. When the volatizing device 100 is operated, a user may inhale a volatized fluid via the mouthpiece 116. The term fluid includes liquids and/or gases which may or may not include suspended fine particulate solids. Examples of volatized materials which a person may inhale include nicotine, essential oils, elixirs, therapeutic agents, tonics, pharmaceuticals, phyto based constituents and/or other remedies.

The mouthpiece 116 may be the sole or primary exit for volatized materials. If volatization occurs with the mouthpiece 116 either retracted and/or covered, unsafe temperature and/or pressure may build up within the volatizing device 110 and cause a failure. Therefore, the volatizing device 100 may include safety features that prevent operation while the mouthpiece cover 128 is covering or partially covering the mouthpiece 116 and/or when the mouthpiece is retracted or partially retracted within a cavity defined by the front housing 110 and rear housing 112. Such safety features may be mechanically activated and/or electronically activated.

Figure 2:
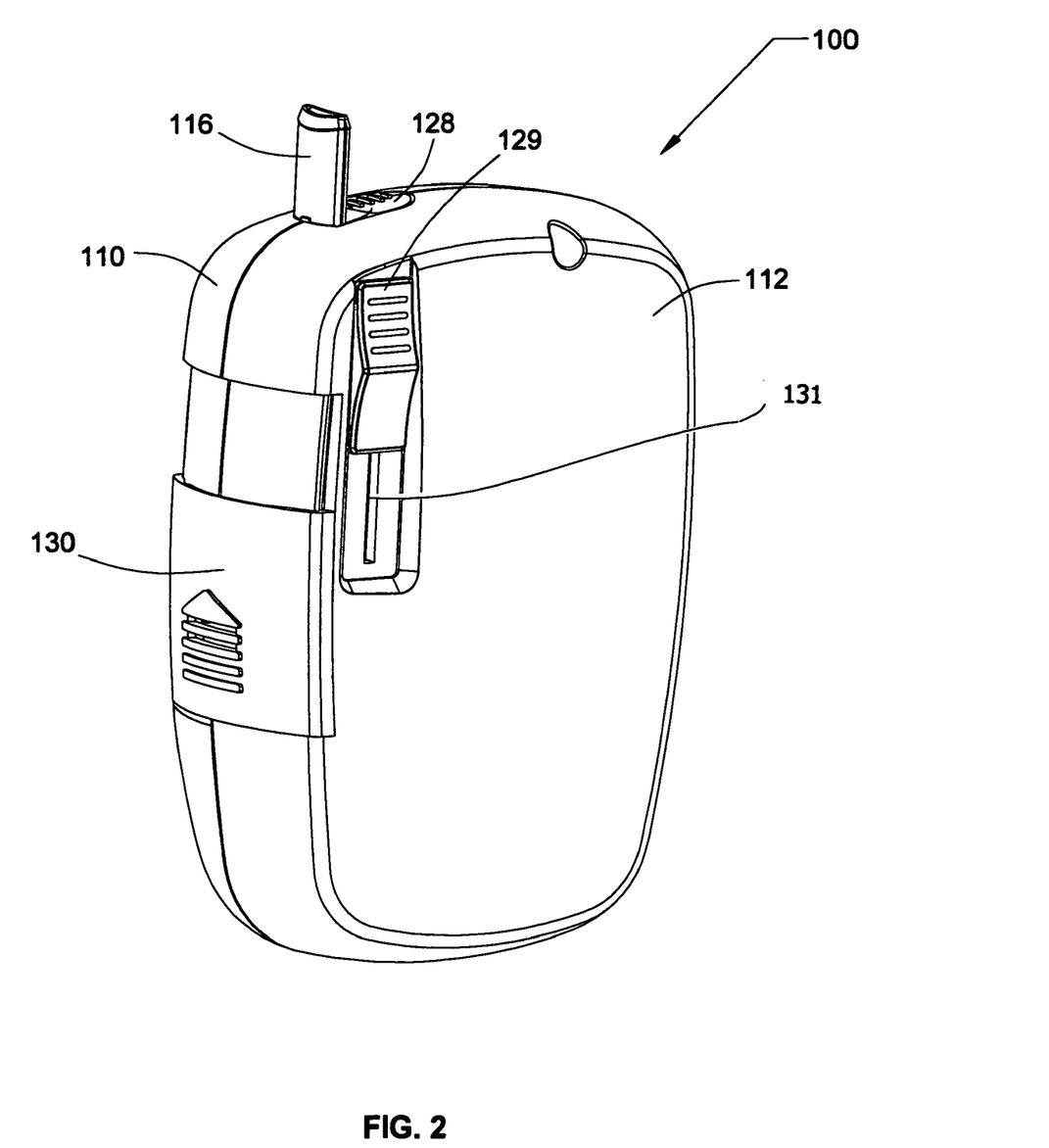
FIG. 2 is a rear perspective view of an inhaler.

Referring now to FIG. 2, there is shown a rear perspective view of the volatizing device 100. In this view, a mouthpiece slider 129 is visible. The mouthpiece slider is an example of a mechanical device which may displace the mouthpiece 116. The mouthpiece slider 129 may be attached to or integral to the mouthpiece 116. The mouthpiece slider 129 may be adapted to slide through a slot 131. The slot 131 may be defined by the rear housing 112, the front housing 110 (not shown) or other portion of the volatizing device 100. Other examples (not shown) of mechanical devices that may displace the mouthpiece 116 include winding knobs, springs, belts, wheels and other devices.

A sensor (not shown) may detect whether the mouthpiece 116 is extended or not. This sensor may be used to control whether some or all functions of the volatizing device 100 are operable. For example, while the device may be able to power up when the mouthpiece 116 is extended, volatization may be restricted. As a safety precaution, extension of the mouthpiece 116 coupled with switching of the power button 118 may both be required for activation of the volatization device 100.

The heating chamber cover 130 is a cover adapted to at least partially conceal and/or enclose an aperture (not shown) in the front housing 110 and/or the rear housing 112 at a location proximate to a heating chamber (described below). The heating chamber cover 130 may be displaceable relative to the front housing 110, the rear housing 112, another portion of the volatizing device 100 or combinations thereof.

In FIG. 2, the heating chamber cover 130 is shown in a closed position. The term closed refers to the blocking, preventing, or obstruction of access to the interior or contents of a structure. The term position refers to an arrangement of parts in relation to one another or to an external source of orientation or reference.

Figure 5:
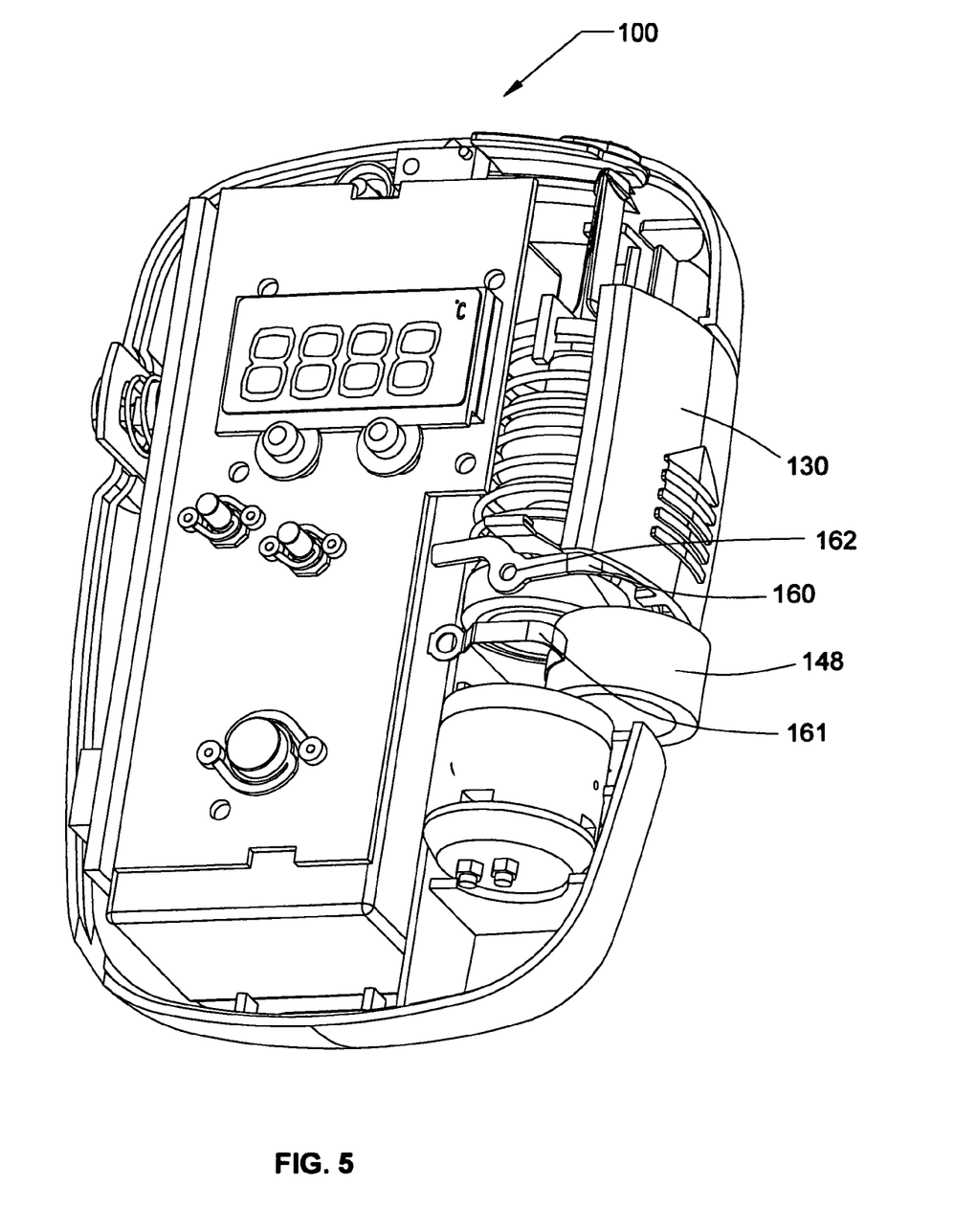
FIG. 5 is a front perspective view of an inhaler with a cover removed.

The heating chamber cover 130 may be displaced from the closed position to an open position. Referring briefly to FIG. 5, there is shown a front perspective view of an inhaler with a cover removed. In FIG. 5, the heating chamber cover 130 is in an open position, and a heating chamber 148 is accessible to a user of the volatizing device 100. Although the heating chamber cover 130 is shown as a device which slides among open and closed positions, the heating chamber cover 130 may be displaced among open and closed positions via rotations, which may include hinges, pins, pivots or other rotating devices, notches, snapping on and off and other electrical and/or mechanical methods.

The heating chamber cover 130 may provide protection to the user such that when the volatizing device 100 is being operated, the user and/or materials proximate the volatizing device 100 are not subjected to burns and/or fire. Such protection may be achieved by providing a heat insulation barrier between the heating chamber 148 and the exterior of the volatizing device 100.

As volatization is a process which requires heat, the heating chamber 148 may achieve harmful temperatures. As a safety feature, the heating chamber cover 130 may lock in position relative to the volatizing device 100 if the heating chamber 148 exceeds a predetermined temperature. A predetermined temperature may be selected as 120° F. or another temperature. The term lock refers to fastening together or closing of one thing relative to another. The term fasten refers to causing parts which are separate to hold together. The locking feature may be achieved via expansion of coupled materials, a latch, a cam, a gear, electronic controls or other means. Thus, the locking feature may prevent burns, fires and/or other harm.

The power button 118, the temperature increase button 120, the temperature decrease button 122, and a heater button 124 (FIG. 3) may be push-button switches. The term switch refers to a device for making, breaking, opening, closing, or modifying the connections of an electrical circuit. A button or push-button is a type of switch which may have the shape of a disk, ball, other shape that is able to be pushed, indented, or deformed inward by a person's finger, thumb or hand.

Figure 3:
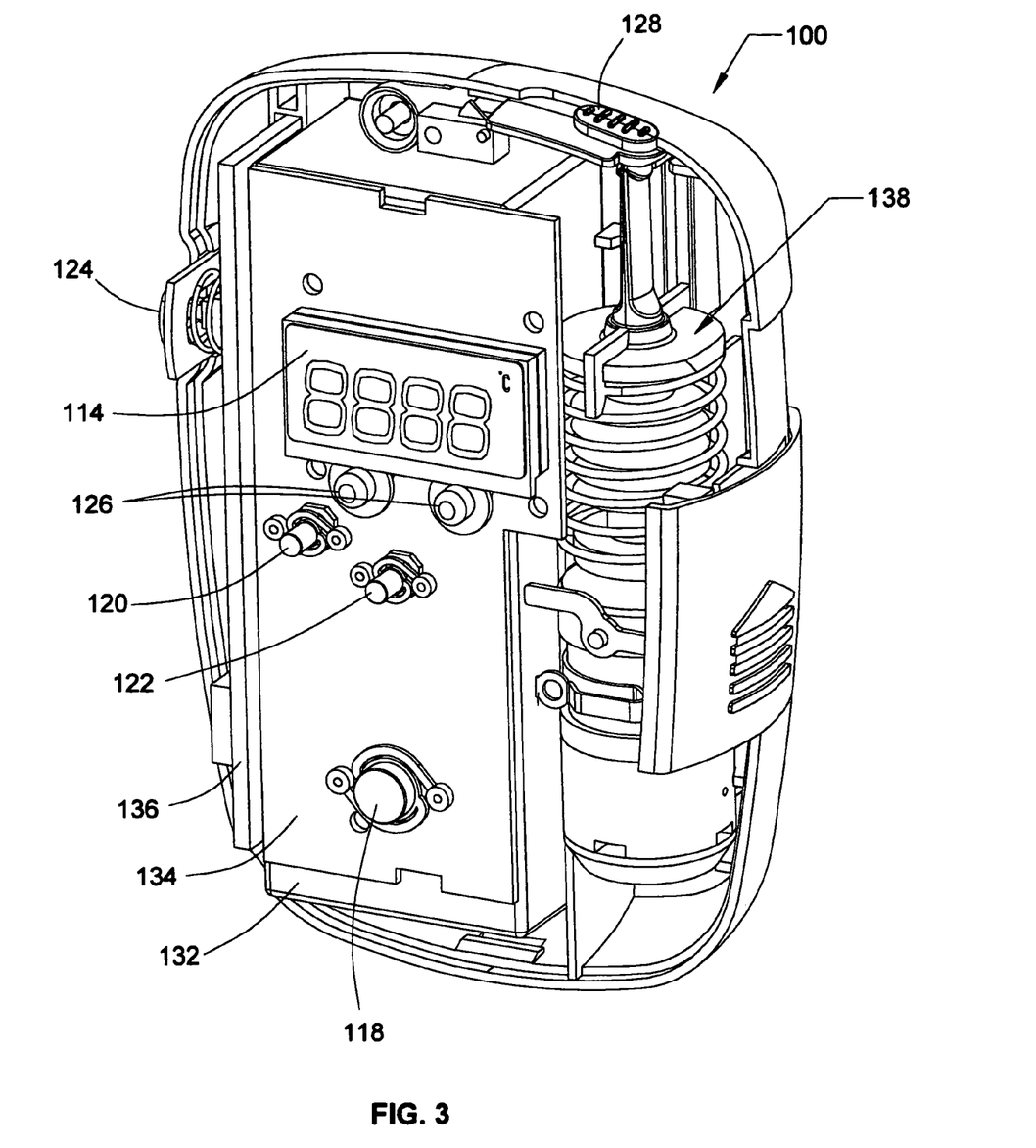
FIG. 3 is a front perspective view of an inhaler with a cover removed.

The power button 118, the temperature increase button 120, the temperature decrease button 122, and the heater button 124 may be other types of switches. The location of the switches may be selected based on ease of operation and ergonomics while holding the volatizing device 100 in a single hand. Thus, the switches may all be located on the front housing 110 or the rear housing 120. The front housing 110 and the rear housing 120 may be designed such that when assembled, they form, in combination, a plurality of sides (not shown). For example, the front housing 110 and the rear housing 120 may define an elongate rectangular solid, a cylinder, a sphere or other geometry. Thus, an example the heater button 124 may be disposed on a left side of the volatizing device 100 as shown in FIG. 3.

To promote safe operation, the location of the switches may be distributed around the volatizing device 100 in order to prevent accidental activation. Although the power button 118 may serve as the primary switch for enabling the volatizing device 100, additional switches may be required to be activated simultaneously and/or in a timed sequence to activate the volatizing device 100.

Moreover, the power button 118, the temperature increase button 120, the temperature decrease button 122 and the heater button 124 may be a single switch (not shown) that interacts with a controller (not shown) and the display 114. In such an embodiment, a user of the volatizing device 100 may have the ability to scroll through menus and enter various information to control the volatizing device 100. Such information may include the user's name, password, type of material to be volatized, amount of material to be volatized, heat and temperature parameters for volatization, time, date, and other information.

A display is a device which provides a visual image. Examples of displays include light emitting diodes (LED), liquid crystal displays (LCD) and other display types. Additional examples of displays include a single or plurality of analog gauges, wheels, needle pointers and other mechanical indicators. The display 114 may be disposed on, within or behind the front housing 110, the rear housing 112 or both. The display 114 may be a single unit or a combination of display units (not shown). The display 114 may have dimensions and geometry that are familiar to users of handheld devices. For example, the display 114 may have a width of 2 inches and a length of 4 inches, or other dimensions. The display 114 may provide various information including the temperature within a heating chamber (discussed below).

The indicator lights 126 may be separate or distinct from the display 114. The indicator lights 126 may provide information that indicates that a battery (not shown) has sufficient charge to perform a volatization operation. The indicator lights 126 may illuminate when the unit is ready to volatize a material or is actively volatizing a material. The indicator lights 126 may identify an unsafe condition and indicate an automatic shutdown, for example excessive heat or battery failure. The indicator lights may be disposed proximate the display 114 or near one of the switches, for example the power button 118, or other location.

The volatizing device 100 may include an illuminator (not shown), for example a small light bulb or LED, which may temporarily illuminate the display 114 should the operating environment be dim or dark. Additionally, the display 114 may be designed to support Braille. Such an embodiment may include a plurality of small dots, disks or balls that variably protrude from the display in order to communicate information to a blind person. Additionally, the display 114 may be designed to support sound. Such an embodiment may include a speaker or other sound emitting device.

Figure 7:
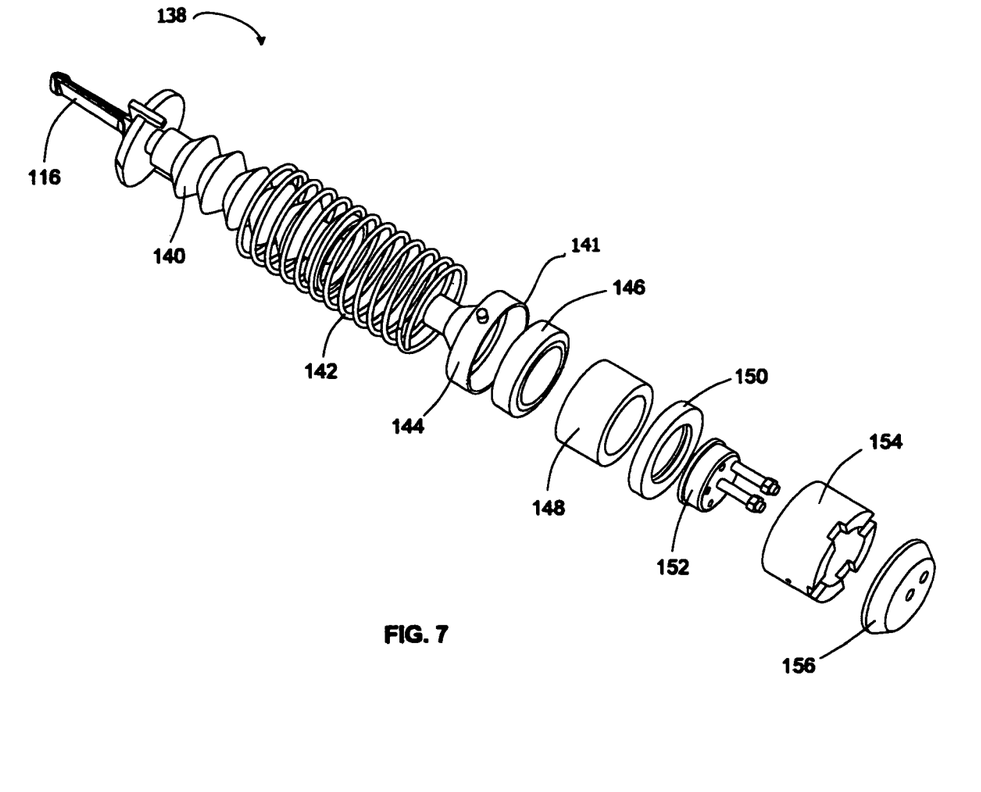
FIG. 7 is a perspective exploded view of a volatization assembly.
Figure 8:
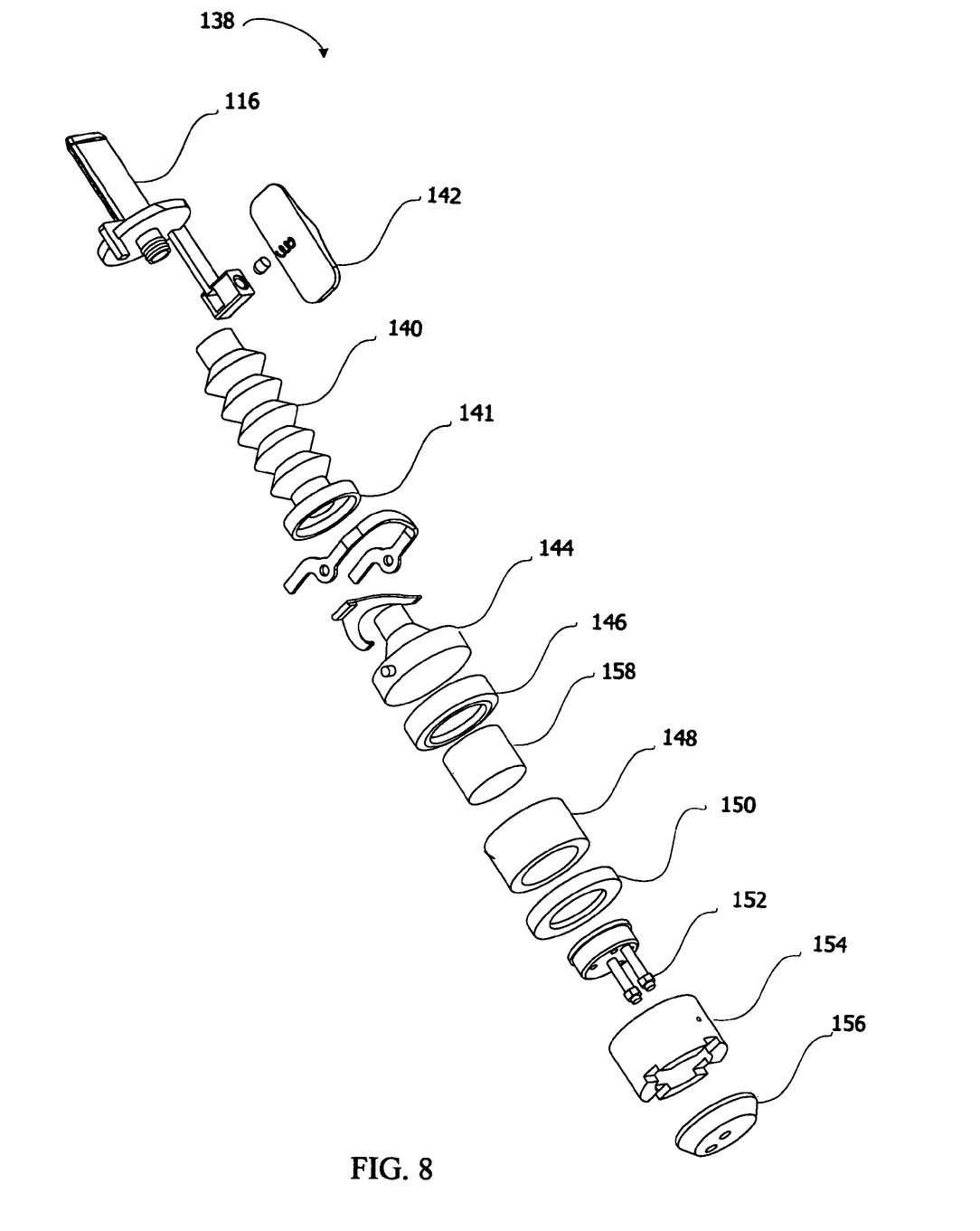
FIG. 8 is a perspective exploded view of a volatization assembly.

Referring now to FIG. 7 and FIG. 8, there are shown perspective exploded views of a volatization assembly 138. The volatization assembly 138 may include the mouthpiece 116, a vapor tube 140, a mouthpiece extension device 142, a chamber lid 144, an upper seal 146, a heating chamber 148, a lower seal 150, a heating element 152, a heating element housing 154, and a heating element cover plate 156. The majority of the volatization assembly 138 may be disposed within a cavity defined by the front housing 110 and the rear housing 112. However, some portions of the volatization assembly 138 may extend outside of the front housing 110 and the rear housing 112.

The mouthpiece 116 may be disposed at one end of the volatization assembly 138. The mouthpiece 116 may be attached to, integral with or abut the vapor tube 140. The mouthpiece 116 and the vapor tube 140 may, in combination, define a cavity for fluids to flow therethrough. Thus, the mouthpiece 116 may receive a volatized material in fluid form via the vapor tube 140.

The vapor tube 140 may be expandable. The term tube refers to a hollow elongated body that is adapted to convey fluids. The term expandable refers to the ability to modify a body's shape such that the modified body has a larger volume than the original body. For example, the vapor tube 140 may expand via bending, folding, elongating, or stretching. The vapor tube 140 may also be adapted to retract, contract or compact to a smaller size and volume.

The mouthpiece extension device 142 is a member that assists in displacing the mouthpiece 116 and/or the vapor tube 140. The mouthpiece extension device 142 may be integral to, attached to, or abut the mouthpiece slider 129 (FIG. 2). The mouthpiece extension device 142 may be integral to, attached to, or abut either the mouthpiece 116 or the vapor tube 140. The mouthpiece extension device 142 may be embodied as a spring as shown in FIG. 7, as a lever as shown in FIG. 8 or another member. The mouthpiece extension device 142 may be displaced upward to shift the mouthpiece 116 into an extended position when the mouthpiece cover 128 is in the open position.

Disposed from top to bottom between the vapor tube 140 and the heating element 152 may be a chamber lid 144, an upper seal 146, a heating chamber 148 and a lower seal 150.

The chamber lid 144 may be integral to, attached to, or abut an opening 141 of the vapor tube 140. The chamber lid 144 and the vapor tube 140 may at least partially define a cavity through which a fluid may flow. Thus, the vapor tube 140 may receive a volatized material via the chamber lid 144.

The upper seal 146 may be disposed between the chamber lid 144 and the heating chamber 148. The upper seal 146 may be integral to, attached to, or abut one or both of the chamber lid 144 and/or the heating chamber 148. The upper seal 146 may have a permeable surface and/or at least partially define a cavity along with the chamber lid 144. Thus, the chamber lid 144 may receive a volatized material via the upper seal 146.

The upper seal 146 and the lower seal 150 may include a mesh, filter, or screen to prevent non-vapor or solid material from passing from the heating chamber 148 to either the chamber lid 144 or the heating element 152. Using a mesh, filter, or screen may prevent loose tobacco or herbs from coming in contact with the heating element 152 resulting in ignition. Additionally, the mesh, filter, or screen may prevent solid particulate matter from being inhaled by a human or other mammal and/or emitted into the environment.

The lower seal 150 may be disposed between the heating chamber 148 and the heating element housing 154. The lower seal 150 may abut, be integral with or attached to the heating chamber 148 and the heating element 152 and/or the heating element housing 154. The lower seal 150 may be permeable to fluids.

The heating element 152 may be disposed at least partially within the heating element housing 154. The heating element 152 may include an electrical resistive material, for example, an aluminum alloy, a ferrous alloy, carbon filament yarns, and equivalents thereof similar to the materials used in an electrocautery surgical tool, a heating element of an automotive cigarette lighter, or an electric stove heating element. Additionally, the heating element 152 may include a honeycomb ceramic heating element, an infrared heating element, and/or an inductive heating element. The term heating element refers to a component which radiates heat based at least in part on a chemical reaction, electrical resistance, friction, electromagnetic fields, inductance or other physical effect.

The heating element cover plate 156 may be disposed abutting, integral to, or attached to an end of the heating element housing 154. The heating element housing 154 and the heating element cover plate 156 may include a heat resistant material with insulating properties. Heat resistant materials include ceramics, sintered metals, composites, fabrics and other materials.

Figure 6:
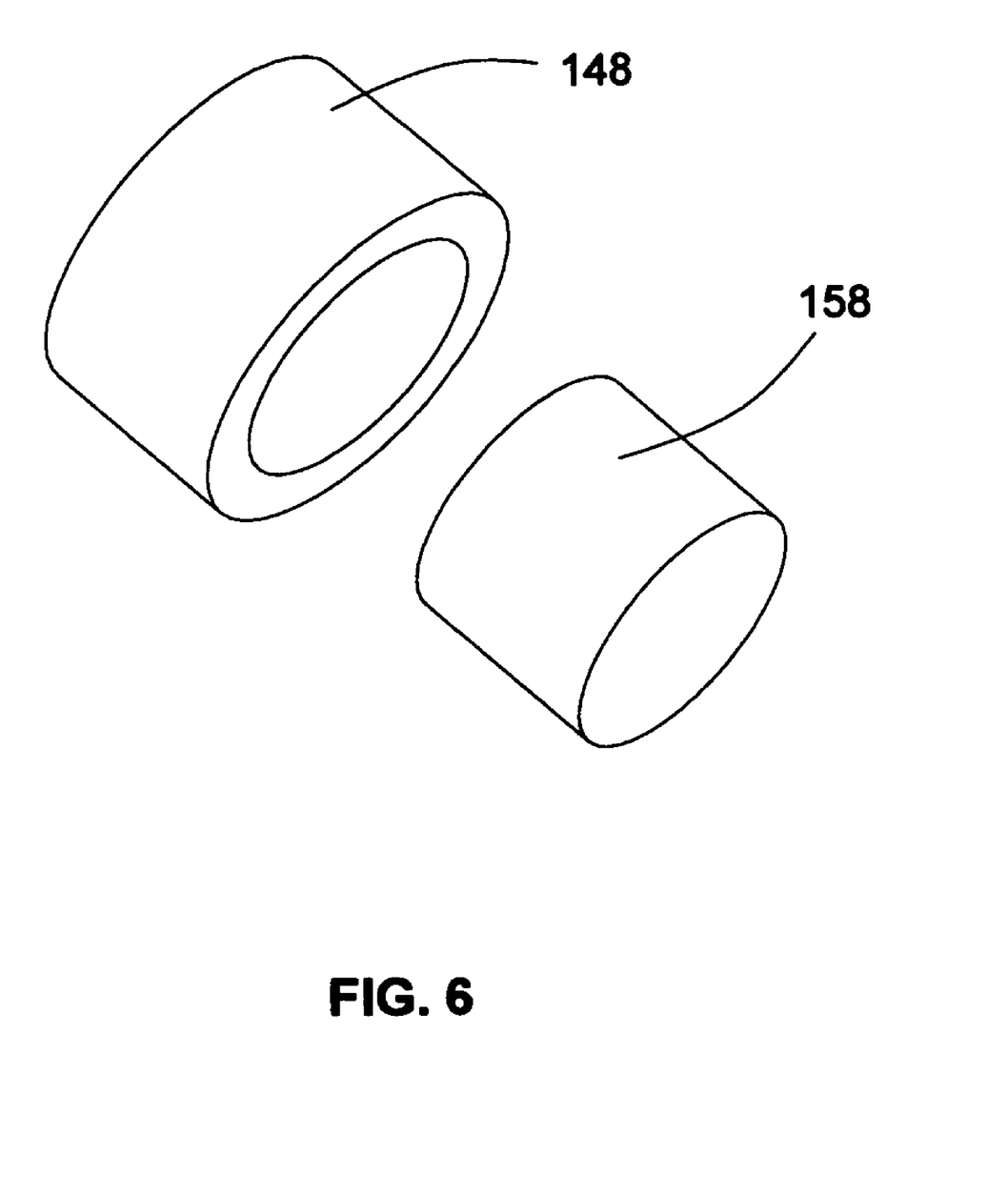
FIG. 6 is a plan view of a heating chamber and consumable product.

Referring now to FIG. 6, there is shown the heating chamber 148 and a consumable product 158. The heating chamber 148 may at least partially define a cavity. The heating chamber 148 may have the geometry of a hollow sphere, rectangular solid, cylinder or other shape. The consumable product of FIG. 6 is a constituent 158. The constituent 158 may be a phyto material or essential oil. The constituent 158 may be formed and adapted for being disposed within the heating chamber 148. Examples of a constituent are a pre-formed cartridge of tobacco, a compressed matrix of material similar to a medicine tablet, or a matrix of material similar to a sponge, surgical cotton, compressed surgical cotton or gauze used to hold a liquid form of constituent, essential oils, or herbs.

Unlike smoking where 80%–90% of the essential ingredients are burned off and never absorbed by the lungs, volatization is very efficient. Thus, the quantity of a phyto material, such as tobacco, to satisfy a user may be substantially less than that in a cigarette or cigar. Hence, a user may save money by not purchasing as much tobacco. Moreover, the volatization process releases substantially less byproducts into the environment as the majority of a volatized material is transferred directly to a user's lungs. In turn, second hand smoke and foul odor issues may be substantially eliminated.

Each volatization operation may correspond to an inhalation of a fluid. The number of inhalations per constituent 158 may depend upon the nature of the constituent, the moisture content of the constituent, and the user's lung capacity. For some materials or constituents, one or two inhalations may be all that is necessary to extract all of the essential ingredients. Other constituents, tobacco for example, may require multiple inhalations.

Many phyto materials volatize between 100 and 150 degrees Celsius. The nicotine in tobacco, for example, vaporizes between approximately 180 and 200 degrees Celsius. Volatile oils such as camphor and mint vaporize at as low as 30 to 60 degrees Celsius. Some medicinal herbs vaporize at 190 to 210 degrees Celsius. However, the moisture content and ambient pressure may determine the ideal volatization conditions. Many phyto materials ignite at 235° C. Thus, a predetermined maximum temperature for the heating chamber 148 may be set at 230° C. or other temperature.

The heating chamber 148 may include a heat resistant material with insulating properties. The term chamber refers to a structure which at least partially encloses a space designed for a special purpose, such as volatizing or heating. The heating chamber 148 may have a cylindrical form with open ends, a spherical mesh, a porous cube or other geometry. The cross section of the heating chamber 148 may have a rectangular, circular, triangular or other shaped geometry. The size of the heating chamber 148 may be selected based on the number of volatizations a given quantity of constituent may be used for. For example, a one gram sample of constituent, which may require 500 cubic millimeters or other volume, may provide multiple doses or inhalations of volatized material.

Referring now to FIG. 8, the volatizing device 100 may include a sensor (not shown). The term sensor refers to a device designed to respond to a physical stimulus and transmit a resulting signal. The term signal refers to a detectable physical quantity or impulse, such as a voltage, current, or magnetic field strength. Examples of sensors include temperature sensors, pressure sensors, mass sensors, displacement sensors, and other sensors.

The sensor (not shown) may be disposed proximate the heating element 152. The term proximate refers to being physically very near. The sensor (not shown) may provide a signal to a controller (described below). Thus, the controller may monitor the temperature of the heating element 152. Additional sensors may be disposed within the heating chamber 148, upstream and/or downstream of the heating chamber 148 and/or exterior or integral to the front housing 110 or rear housing 112. Such sensors may provide the controller with data regarding the ambient environmental conditions, the parameters of the heating element 152, the heating chamber 154, the constituent 158, the volatized fluid (not shown), and other elements of the volatizing device 100.

Referring again to FIG. 5, the volatizing device 100 may include an extractor 160, an extractor spring 161, and an extractor pivot 162. The extractor 160, extractor spring 161 and extractor pivot 162, in combination, form an embodiment of an ejector. The term ejector refers to a device that drives something out or physically displaces something. An ejector may be electronically and/or mechanically activated. Examples of ejectors include levers, slides, springs, and displaceable magnets.

With respect to the ejector of FIG. 5, when the heating chamber cover 130 is shifted to an open position such that the heating chamber 148 is exposed, the extractor 160 rotates about the extractor pivot 162. In turn, the ejector lifts the upper seal 146, and the extractor spring 161 ejects the heating chamber 148 from the volatization assembly 138.

Figure 4:
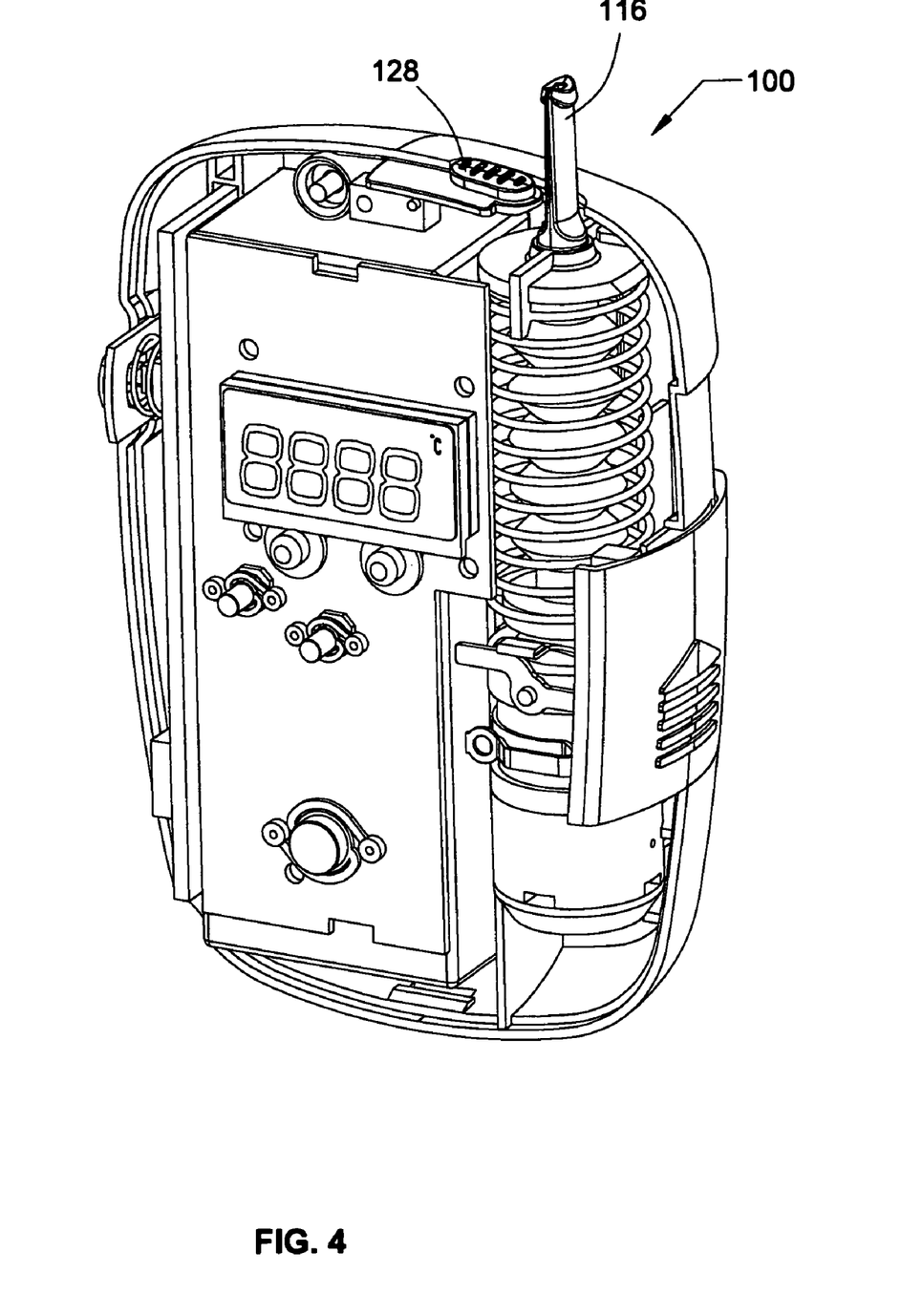
FIG. 4 is a front perspective view of an inhaler with a cover removed.

Referring to FIGS. 3, 4, and 5, there is shown a front perspective view of an inhaler with a cover removed. The volatizing device 100 may include a battery 132, a front circuit board 134, a side circuit board 136, and the volatization assembly 138.

The battery 132 may be supplemented with or substituted with a USB power source, a solar cell, a vehicle's accessory power source, a household AC power or other power source. The term battery refers to a cell, group of cells, electrical device or system which converts stored chemical and/or mechanical energy into electrical energy by a reversible chemical and/or mechanical process, and can provide electrical power to a circuit or system. The battery 132 may have a geometry to provide easy installation and replacement. Examples of batteries include alkaline, nickel cadmium, nickel metal hydride, lithium ion, polymer lithium ion, and other materials. The battery 132 may be rechargeable and/or disposable.

The battery 132 may be recharged by installing the volatizing device 100 into a recharging cradle (not shown) or by plugging a power cord into a power connector (not shown). When the volatizing device 100 is being charged, the indicator light 126 and/or the display 114 may identify that the volatizing device is being charged. Such identification may be via a flashing LED or display of a string of characters such as "charging." Additional embodiments of indication include illuminating unique colors for charge state. For example, red may indicate charging is in process and green may indicate charging is complete.

The front circuit board 132 and/or the side circuit board 136 may include a controller. The controller may control operation of the device 100, including how energy is transferred energy to the heating element 152. The term transfer refers to the act of causing energy to pass from one source to another. The term energy refers to a capacity for doing work. The controller may include one or more logic arrays, memories, analog circuits, digital circuits, software, firmware, and processors such as microprocessors, field programmable gate arrays (FPGAs), application specific integrated circuits (ASICs), programmable logic devices (PLDs) and programmable logic arrays (PLAs), an electric device and/or combinations therein. An electric device may include a computing device, a processor, a storage device, a memory or combinations thereof.

A storage device may include a storage media included with or otherwise coupled or attached to a computing device. These storage media include, for example, magnetic media such as hard disks, floppy disks and tape; optical media such as compact disks (CD-ROM and CD-RW) and digital versatile disks (DVD and DVD±RW); flash memory cards; and any other storage media. As used herein, a storage device is a device that allows for reading and/or writing to a storage medium. Storage devices include hard disk drives, DVD drives, flash memory devices, and others.

By data unit, it is meant a frame, cell, datagram, packet or other unit of information.

A "computing device" is a device with a processor and memory that can execute instructions. Computing devices can be, for example, personal computers, video game systems, personal video recorders, digital image recorders, digital video recorders, digital audio recorders, telephones, personal digital assistants (PDAs), and special-purpose devices.

Computing devices may run an operating system, such as Linux, Unix, MS-DOS, Microsoft Windows, Palm OS, and Apple Mac OS X operating systems. The volatizing device 100 may connect to, be integrated with, and/or communicate with one or more computing devices. By having the ability the communicate with other computing devices, the volatization process may be externally controlled or monitored. Moreover, programming the controls of the volatizing device 100 may be performed externally and/or communicated to the controller for standalone operation.

Such communications may be achieved via wired communications, fiber optic communication, and/or wireless communications such as WiFi®, infrared communication, Bluetooth®, WiMax, UHF, VHF, CDMA, TDMA, GSM, or other cellular other wireless communication. The volatizing device 100 may be a component of a computing device. The volatizing device 100 may embody one or more computing device.

The controller may record information. The term record refers to causing information to be registered by a storage device via electrical and/or mechanical means so that the information may be reproduced.

The information may include, but is not limited to, battery life remaining, temperature setting of the heating element 152, temperature setting of the heating chamber 148, number of doses for a current constituent, date, time, date and time last used, and an alarm for next use. Such information may be displayed on the display 114.

The term alarm refers to a device that causes a notice, warning, or announcement that calls attention to a circumstance or event. The alarm for next use may indicate a dispensing time for sensitive medicines to the user. Examples of an alarm include information displayed on the display 114, sound projected from a speaker (not shown), vibration from a vibrating element (not shown), blinking from the indicator lights 126 and combinations therein.

The alarm may activate after a predetermined time period has elapsed. The term elapsed refers to a passing of time.

A volatization assembly is a subset of components of a volatizing device which volatizes a phyto material and allows for the displacement of the resulting fluid to exit the volatizing device. Typical resulting fluids from a volatizing device are inhaled into a user's lungs in a much smoother fashion than typical smoke.

Description of Processes of Operation and Use

Referring again to FIG. 1, the mouthpiece cover 128 may be slid into the open position. The mouthpiece 116 may then be extended outside of a cavity defined by the front housing 110 and rear housing 120. The extension of the mouthpiece 116 may be achieved via a spring mechanism (not shown), the mouthpiece extension lever 129 (not shown), or other process. As a safety feature, when the mouthpiece 116 is in a retracted position, the controller may prevent operation of the volatizing device 100.

Referring again to both FIG. 1 and FIG. 5, the heating chamber 148 may be at least partially ejected from the volatizing device 100 by displacing the heating chamber cover 130.

A user may then remove the heating chamber 148. The user may insert a phyto material, for example, a tobacco cartridge, a loose tobacco or herb into the heating chamber 148. If the phyto material is a machine formed tobacco cartridge, the user may insert the cartridge into the heating chamber 148. The user may center the cartridge in the heating chamber 148 so the ends of the cartridge are flush with the ends of the heating chamber 148. If the phyto material includes loose materials, such as tobacco or herbs, the user may insert the loose phyto material into one of the heating chamber 148 that includes a mesh screen.

A user may then insert the heating chamber 148 into the volatizing device 100. The user may displace the heating chamber cover 130 into a closed or locked position. The user may physically observe a click, snap or resistance indicating proper closure.

The volatizing device 100 may be powered by switching the power button 118. In response, the display 114 may display an alphanumeric message and/or the current temperature to indicate to a user that the power is on. The user may adjust the temperature setting by pressing the temperature increase button 120 or temperature decrease button 122. When the temperature setting is adjusted as desired the existing setting may remain displayed for a predetermined time to allow the user to confirm the temperature setting.

Once the volatizing device 100 has been prepared for operation, for example, a constituent has been loaded in the heating chamber 148, the heating chamber 148 has been loaded in the volatization assembly 138, the heating chamber cover 130 has been closed, the mouthpiece 116 has been extended and the power button 118 has been activated, then the volatization process may commence by activating the heater button 124.

Energy may be transferred to the heating element 152 (FIG. 7) in response to switching and/or sustained depressing the heat activation button 124 (FIG. 3). When the heating chamber 148 achieves the predetermined temperature, the controller, based on a signal provided by a sensor, may cause energy to cease flowing to the heating element 152. Likewise, when the temperature within heating chamber 148 falls below the predetermined temperature, the controller may cause energy to flow to the heating element 152.

While the heater button 124 is depressed, an indicator light 126 may illuminate and/or a temperature may be displayed on the display 114. The controller may prevent energy from being transferred to the heating element 152 when the heating chamber 148 reaches a predetermined temperature, for example 190° C. Thus, a given constituent will not ignite or burn.

During operation, a user may press and hold the heater button 124 for a time sufficient to heat up the heating element 152 and the constituent to a temperature sufficient to volatize or vaporize the constituent.

While holding the heater button 124 the user may apply suction at the mouthpiece 116 by inhaling slightly. The suction from inhaling may introduce ambient air into the heating element housing 154 and through the heating chamber 148. The term ambient refers to surrounding environmental conditions.

Thus, the ambient air may be heated and then aid in volatizing the constituent. The resulting volatized fluid may then pass through the expandable vapor tube 140, through the mouthpiece 116 and into the surrounding environment, a mammal or a human.

After the user has received a desired quantity of volatized fluid, the user may switch the power button 118 to power down the volatizing device 100.

The controller may provide various safety functions. For example, the controller may prevent energy from being transferred to the heating element 152 if the temperature or pressure indicated by one of the sensors exceeds a predetermined value. For example, if the temperature of the heating element 152 exceeds 235° C. or the temperature inside the heating chamber 148 exceeds 230° C., the controller may prevent energy from being transferred to the heating element 152.

Predetermined temperatures or pressures may be selected and/or programmed based on the constituent 158, the heating element 152, the materials which compose the front and rear housings 110, 112 or other parameters. Predetermined temperatures and pressures may be set below the ignition point of a given constituent 158.

Following consumption of a phyto material, the user may desire to remove the volatized phyto material. However, the heating chamber 148 may be at a harmful temperature. The controller and/or a mechanical device (not shown) may cause the heating chamber cover 130 to remain in a locked position until the heating chamber 148 cools to a safe temperature.

Once the heating chamber 148 is relatively cool, the user may remove the heating chamber 148 and then remove the consumed material. Consumed material may be blown out, shaken out, be removed with a cotton swab, a toothpick, a small bristle brush, or other cleanser or device.

The battery 132 may require periodic recharging or replacement. The controller may monitor the charge of the battery 132. If the battery 132 requires recharging, the controller may cause an image to be displayed on the display 114 and/or an indicator light 126 to illuminate a predetermined color and/or blink. Additionally, the controller may cause a speaker (not shown) to emit a pre-recorded message, a chirp or beep. The controller may be adapted to notify the user when the batter has 5 minutes of use remaining or other charge remaining.

To recharge the volatizing device 100, the user may connect the volatizing device 100 via a charging transformer into a standard 120 AC outlet or another power source. During charging, the controller may cause a message to be displayed on the display 114, and/or an indicator light 126 to illuminate or flash. When the battery 132 is fully charged, the controller may cause the user to be so notified.

The controller may prevent the battery from overcharging or undercharging. Such techniques are provided with the use of smart batteries and smart chargers. Thus, the controller may include software that enables the volatizing device 100 to provide smart charger functionality.

Additionally, the controller may prevent energy from being transferred to the heating element 152 if the heating chamber cover 130 is open or if the mouthpiece 116 is in a retracted position. This prevents unintentional heating of the heating element 152 if the heater button 124 is accidentally depressed.

Heating elements, switches and controllers may fail due to rapid cycling. Moreover, rapid cycling of the heating element 154 may cause deformation of structural materials such as the front housing 110 and the rear housing 112. In order to prevent premature failure of the volatizing device 100, the controller may prevent energy from being transferred to the heating element 152 if a predetermined time has not elapsed from the last transfer of energy to the heating element 152.

Closing Comments

The foregoing is merely illustrative and not limiting, having been presented by way of example only. Although examples have been shown and described, it will be apparent to those having ordinary skill in the art that changes, modifications, and/or alterations may be made.

Although many of the examples presented herein involve specific combinations of method acts or system elements, it should be understood that those acts and those elements may be combined in other ways to accomplish the same objectives. With regard to flowcharts, additional and fewer steps may be taken, and the steps as shown may be combined or further refined to achieve the methods described herein. Acts, elements and features discussed only in connection with one embodiment are not intended to be excluded from a similar role in other embodiments.

For any means-plus-function limitations recited in the claims, the means are not intended to be limited to the means disclosed herein for performing the recited function, but are intended to cover in scope any means, known now or later developed, for performing the recited function.

As used herein, "plurality" means two or more.

As used herein, a "set" of items may include one or more of such items.

As used herein, whether in the written description or the claims, the terms "comprising ", "including", "carrying", "having", "containing", "involving", and the like are to be understood to be open-ended, i.e., to mean including but not limited to. Only the transitional phrases "consisting of" and "consisting essentially of", respectively, are closed or semi-closed transitional phrases with respect to claims.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

As used herein, "and/or" means that the listed items are alternatives, but the alternatives also include any combination of the listed items.

The invention claimed is:

1. An apparatus comprising:
a housing adapted to be handheld
a heating element disposed within the housing
a heating element switch electrically coupled with the heating element
a heating chamber disposed within the housing a heating chamber cover, said cover at least partially ejects the heating chamber from the housing when the heating chamber cover is displaced relative to the housing a mouthpiece displaceable relative to the housing, the mouthpiece at least partially defining a cavity, said cavity receives a volatized phyto material a controller electrically coupled with the heating element switch, the controller adapted to control a transfer of energy to the heating element wherein the controller is adapted to prevent the transfer of energy to the heating element if the mouthpiece is not displaced relative to the housing.

2. The apparatus of claim 1 wherein the controller is adapted to prevent the transfer of energy to the heating element if the heating chamber cover is not in a closed position relative to the housing.

3. The apparatus of claim 1 wherein the heating chamber cover is adapted to lock in a closed position relative to the housing when a temperature of the heating chamber is greater than a predetermined temperature.

4. The apparatus of claim 1 further comprising
a storage device adapted to record a time that energy was transferred to the heating element
an alarm adapted to provide a next use reminder based on the time that energy was transferred to the heating element.

5. The apparatus of claim 4 wherein the controller is adapted to prevent the transfer of energy to the heating element if a predetermined time has not elapsed from the time that energy was transferred to the heating element.

6. The apparatus of claim 1 further comprising a tube disposed between the mouthpiece and the heating chamber, the tube adapted to flex, the tube at least partially defining the cavity.

7. The apparatus of claim 1 further comprising a first temperature sensor disposed within the heating chamber, wherein the controller is adapted to prevent the transfer of energy to the heating element if the first temperature sensor provides a first signal indicating at least a first predetermined temperature within the heating chamber.

8. The apparatus of claim 7 further comprising a second temperature sensor proximate the heating element, wherein the controller is adapted to prevent the transfer of energy to the heating element if the second temperature sensor provides a second signal indicating at least a second predetermined temperature proximate the heating element, the second predetermined temperature different than the first predetermined temperature.

9. The apparatus of claim 8 wherein the controller is adapted to prevent the transfer of energy to the heating element if an ambient temperature exterior to the housing exceeds a third predetermined temperature different than both the first and second predetermined temperatures.

10. The apparatus of claim 1 wherein the apparatus is an inhaler device.

* * * * *